United States Patent [19]

Frenette et al.

[11] Patent Number: 4,683,325

[45] Date of Patent: Jul. 28, 1987

[54] LEUKOTRIENE ANTAGONISTS

[75] Inventors: Richard Frenette; Joshua Rokach, both of Laval, Canada; Masatoshi Kakushima, Hirochi, Japan; Robert N. Young, Senneville, Canada

[73] Assignee: Merck Frosst Canada, Inc., Kirkland, Canada

[21] Appl. No.: 661,560

[22] Filed: Oct. 17, 1984

Related U.S. Application Data

[63] Continuation-in-part of Ser. No. 573,169, Jan. 23, 1984, abandoned, which is a continuation-in-part of Ser. No. 546,013, Oct. 27, 1983, abandoned.

[51] Int. Cl.$^4$ ............................................. C07C 149/40
[52] U.S. Cl. ......................................... 560/10; 548/252; 549/299; 558/235; 558/413; 558/414; 560/21; 560/28; 560/34; 560/45; 560/48; 560/53; 560/56; 562/428; 562/436; 562/439; 562/452; 562/457; 562/462; 562/466
[58] Field of Search ....................... 560/53, 56, 10, 21, 560/28, 34, 45; 562/462, 428, 466, 436, 439, 452; 260/465 D; 514/510, 520

[56] References Cited

U.S. PATENT DOCUMENTS 3,954,852  5/1976  Shen ............................... 560/56
4,125,732  11/1978  McEvay ........................... 560/56
4,443,626  4/1984  Noda ............................... 562/462

FOREIGN PATENT DOCUMENTS 56172  7/1982  European Pat. Off. .
61800  10/1982  European Pat. Off. .
2058785  4/1981  United Kingdom .

OTHER PUBLICATIONS

Murch, "Advanced Organic Chemistry; Reactions Mechanisms, and Structure," pp. 357–361 (1968).
D. M. Bailey et al., Ann Rpts. Med. Chem 17 203 (1982).
B. Samuelson, Science, 220 568 (1983).
J. Med. Chem., vol. 20, 371 (1977).

*Primary Examiner*—Michael L. Shippen
*Attorney, Agent, or Firm*—Gabriel Lopez; Hesna J. Pfeiffer; Paul H. Ginsburg

[57] ABSTRACT

Compounds having the formula:

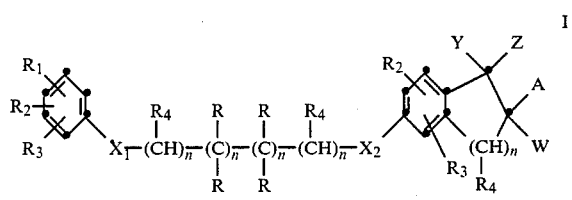

are antagonists of leukotrienes of $C_4$, $D_4$ and $E_4$, the slow reacting substance of anaphylaxis. These compounds are useful as anti-asthmatic, anti-allergic, anti-inflammatory and cytoprotective agents.

12 Claims, No Drawings

LEUKOTRIENE ANTAGONISTS

This application is a continuation-in-part of U.S. Ser. No. 573,169, filed Jan. 23, 1984, now abandoned, which is a continuation-in-part of U.S. Ser. No. 546,013, filed Oct. 27, 1983 now abandoned.

This invention is directed to compounds which act as antagonists of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., *Ann. Rpts. Med. Chem.* 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate musous production and could be an important mediator of neutrophil and eosinophil accumulation in asthmatic lungs. 5-Lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. Leukotrine antagonists would therefore be a new class of drugs for the treatment of asthma.

Psoriasis is a human skin disease which effects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function. See for example, B. Samuelson, *Science,* 220, 568 (1983).

Several classes of compounds exhibit ability to antagonize the action of leukotrienes in mammals, especially humans. See for example: Great Britain Patent Specification No. 2,058,785; and European Patent Application Nos. 56,172 and 61,800.

The present invention provides compounds that act as antagonists to prevent leukotriene action or as inhibitors to prevent synthesis. These compounds may be administered by insufflation, intravenously, rectally, topically, orally, parenterally including subcutaneously and intramuscularly, or nasally. The present invention also provides methods for the preparation of these compounds. The present invention also provides intermediates useful in the synthesis of these compounds. The present invention also provides pharmaceutical formulations for administering these compounds.

The compounds of the present invention may be used to treat or prevent mammalian (especially human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induces renal failure.

The present invention relates to compounds having activity as leukotriene antagonists, to methods for their preparation, to intermediates useful in their preparation and to methods for using these compounds. Because of their activity as leukotriene antagonists, the compounds of the present invention are useful as anti-asthmatic, anti-allergic, and anti-inflammatory agents and are useful in treating allergic rhinitis and chronic bronchitis and for amelioration of skin diseases like psoriasis and atopic exzema. These compounds are also useful to antagonize or inhibit the pathologic actions of leukotrienes on the cardiovascular and vascular systems.

The compounds of the present invention have the formula:

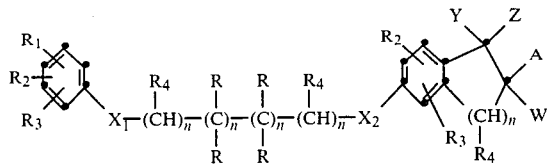
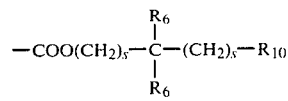

wherein
- each R is independently H, OH, OR$_2$ or together they form the group, =C(R$_4$)$_2$;
- R$_1$ is H, OH, acyl, formyl, R$_5$CO, or R$_5$OCO;
- each R$_2$ and each R$_3$ is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; N(R$_4$)$_2$; COOR$_4$; CH$_2$OR$_4$; formyl; CN; trifluoromethylthio; or nitro;
- each R$_4$ is independently H or alkyl of 1 to 6 carbon atoms which may be straight chain or branched;
- X$_1$ and X$_2$ are each independently oxygen, sulfur, sulfoxide, sulfone;

wherein R$_5$ is alkyl of 1 to 6 carbon atoms which may be straight chain or branched; NR$_6$;

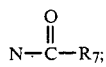

N-CN; or NCONHR$_6$;
- each R$_6$ is independently H or alkyl of 1 to 6 carbon atoms which may be straight chain or branched;
- each R$_7$ is independently alkyl of 1 to 6 carbon atoms which may be straight chain or branched, or alkoxy of 1 to 6 carbon atoms which may be straight chain or branched;
- Y is H or is combined with Z to be doubly bonded oxygen or is combined with W to be a bond;
- W is H, R$_4$ or is combined with Y to be a bond;
- Z is combined with Y to be doubly bonded oxygen or is H, OH or OR$_4$;
- A is —(C(R$_4$)$_2$)$_s$—R$_8$ wherein s is 0 to 3 and R$_8$ is COOR$_4$; CH$_2$OH; CHO; tetrazole; NHSO$_2$R$_9$; CONHSO$_2$R$_9$; hydroxymethylketone; CN; CON(R$_7$)$_2$; a monocyclic or bicyclic heterocyclic ring containing an acidic hydroxyl group; or $$-COO(CH_2)_s-\underset{\underset{R_6}{|}}{\overset{\overset{R_6}{|}}{C}}-(CH_2)_s-R_{10}$$

wherein each s is independently 0 to 3; and R$_{10}$ is
- (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
- (B) the radical X'-R$_{11}$ wherein X' is O, S or NH and R$_{11}$ contains up to 21 carbon atoms and is (1) a hydrocarbon radical or (2) an acyl radical of an organic acyclic or monocyclic carboxylic acid containing not more than 1 heteroatom in the ring;
- each n is independently 0, 1, 2 or 3;
- R$^9$ is OH, alkyl or alkoxy of 1 to 6 carbon atoms, perfluoroalkyl of 1 to 6 carbon atoms, phenyl or phenyl substituted by one or more R$_2$ groups;
- and a pharmaceutically acceptable salt or acid addition salt thereof.

When Z is OH and A is a carboxylic acid (or a derivative thereof) it will be evident to the skilled artisan that such a compound may form a lactone structure, as illustrated in Scheme III. These lactone derivatives are included within the scope of the present invention.

Preferred compounds of the present invention have the formula Ia:

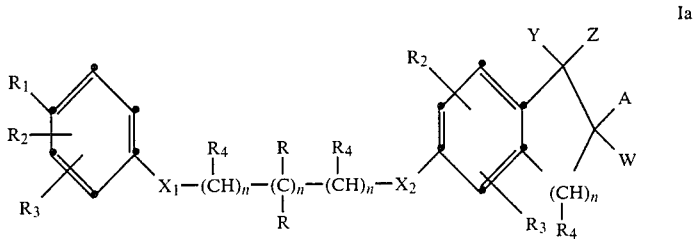

wherein
- each R is independently H, OH, OR$_2$ or together they form the group, =C(R$_4$)$_2$;
- R$_1$ is H, OH, R$_4$CO;
- each R$_2$ and each R$_3$ is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; N(R$_4$)$_2$; COOR$_4$; CH$_2$OR$_4$; formyl; CN; trifluoromethylthio; or nitro;
- each R$_4$ is independently H or alkyl of 1 to 6 carbon atoms which may be straight chain or branched;
- X$_1$ and X$_2$ are each independently oxygen, sulfur, sulfoxide or sulfone;
- each R$_6$ is independently H, alkyl of 1 to 6 carbon atoms which may be straight chain or branched;
- each R$_7$ is independently alkyl of 1 to 6 carbon atoms which may be straight chain or branched, or alkoxy of 1 to 6 carbon atoms which may be straight chain or branched;
Y is H or is combined with Z to be doubly bonded oxygen or is combined with W to be a bond;
W is H, $R_4$ or is combined with Y to be a bond;
Z is combined with Y to be doubly bonded oxygen or is H, OH or $OR_4$;
A is $-(C(R_4)_2)_s-R_8$ wherein s is 0 to 3 and $R_8$ is $COOR_4$; $CH_2OH$; CHO; tetrazole; $NHSO_2R_9$; $CONHSO_2R_9$; hydroxymethylketone; CN; or $CON(R_7)_2$;
each n is independently 0, 1, 2 or 3;
$R^9$ is OH, alkyl or alkoxy of 1 to 6 carbon atoms, perfluoroalkyl of 1 to 6 carbon atoms, phenyl or phenyl substituted by one or more $R_2$ groups.

More preferred compounds of the present invention have the formula Ib:

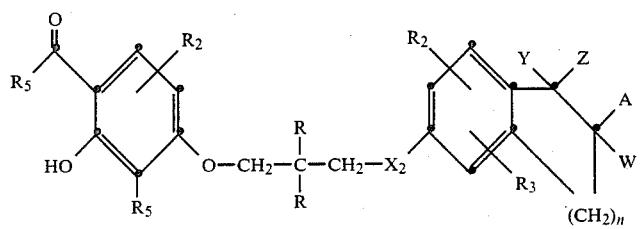

wherein
each R is independently H, OH, $OR_2$ or together they form the group, $=C(R_4)_2$;
each $R_2$ and each $R_3$ is independently H, OH, alkyl of 1 to 6 carbon atoms which may be straight chain or branched; alkenyl of 2 to 6 carbon atoms which may be straight chain or branched; trifluoromethyl; alkoxy of 1 to 6 carbon atoms which may be straight chain or branched; SH; thioalkyl of 1 to 6 carbon atoms which may be straight chain or branched; phenyl; phenyl substituted by alkyl of 1 to 3 carbon atoms or by halogen; benzyl; phenethyl; halogen, amino; $N(R_4)_2$; $COOR_4$; $CH_2OR_4$; formyl; CN; trifluoromethylthio; or nitro;
each $R_4$ is independently H or alkyl of 1 to 6 carbon atoms which may be straight chain or branched;
$X_2$ is oxygen, sulfur, sulfoxide, or sulfone;
$R_5$ is alkyl of 1 to 6 carbon atoms which may be straight chain or branched;
each $R_7$ is independently alkyl of 1 to 6 carbon atoms which may be straight chain or branched, or alkoxy of 1 to 6 carbon atoms which may be straight chain or branched;
Y is H or is combined with Z to be doubly bonded oxygen or is combined with W to be a bond;
W is H, $R_4$ or is combined with Y to be a bond;
Z is combined with Y to be doubly bonded oxygen or is H, OH or $OR_4$;
A is $-(C(R_4)_2)_s-R_8$ wherein s is 1 to 3 and $R_8$ is $COOR_4$; $CH_2OH$; CHO; or tetrazole; and
n is 1, 2 or 3.

All of the above definitions contemplate that, unless otherwise indicated, each $R_4$ and each $R_7$ in groups such as $=(R_4)_2$, $N(R_4)_2$ or $CON(R_7)_2$ are independently selected from the given possible atoms or groups.

SCHEME I

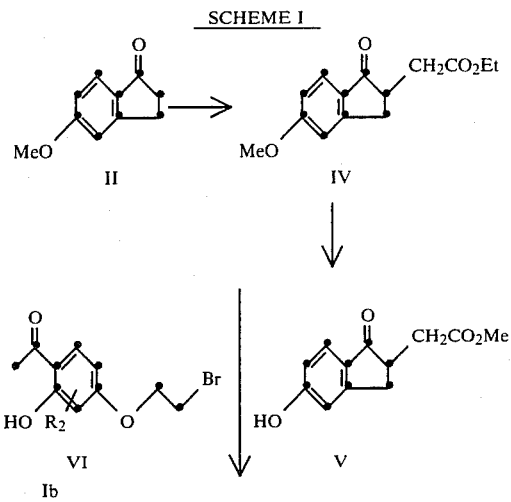

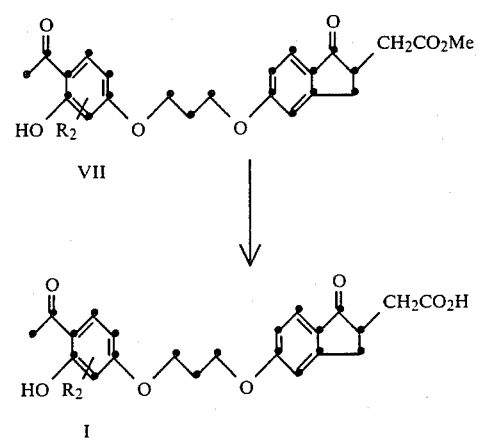

The compounds of the present invention may be prepared by several different routes. According to one method, illustrated in Scheme I, a compound of formula II is reacted with ethyl bromoacetate in the presence of a base such as LDA, KH, or $KN(SiMe_3)_3$ to yield ethyl 5-methoxy-1-indanone-2-acetate, formula IV. Treatment of compound IV with (a) HBr/AcOH and (b) HCl/MeOH affords the 5-hydroxy-indanone compound of formula V.

Reaction of the compound V with the bromide of compound VI or its corresponding chloride or iodide, in the presence of a base, such as potassium carbonate, in a solvent such as methyl ethyl ketone, affords the compound VII. Other suitable bases are alkali metal carbonates such as $Li_2CO_3$, or $Na_2CO_3$. The reaction may also be carried out in other solvents such as THF, monoglyme, diglyme, acetone, or DMF. The temperature range to carry out this transformation is 25°–160° C., the optimum being 60°–70° C.

The ester compound of formula VII is readily hydrolyzed to form the desired carboxylic acid of formula I by treatment with dilute aqueous base, for example, 1N NaOH followed by acidification with aqueous mineral acid, for example, aqueous HCl.

In addition to 5-methoxy-1-indanone, other similar compounds may be employed as starting materials in Scheme I reactions. For example, 5-methoxy-1-indanone-3-acetic acid may be substituted for compound IV in Scheme I, esterified using 10% HCl/MeOH, forming the 3-methyl acetate isomer of the compound of formula V. In addition, 5,6- or 7-methoxy-1-tetralone compounds are commercially available (Aldrich) and may be readily substituted for the compound of formula II in Scheme I.

already used successfully for reacting compounds V and VI. The compound VIII is readily available by reaction of compound V with dimethylthiocarbamoyl chloride in the presence of a base such as pyridine, $K_2CO_3$, or NaH, followed by heating the unisolated intermediate to 200° C. The thiol compound is available from VIII by hydrolysis. The intermediate ester of structure IX is then hydrolyzed to I by reacting it with a base followed by treatment with an acid. The corresponding sulfone of formula I(a) is available through the oxidation of compound IX with m-chloroperbenzoic acid (m-CPBA) and by hydrolysis of the sulfone of formula X.

In addition to the thiol compound of formula VIII, the corresponding tetralone compounds previously

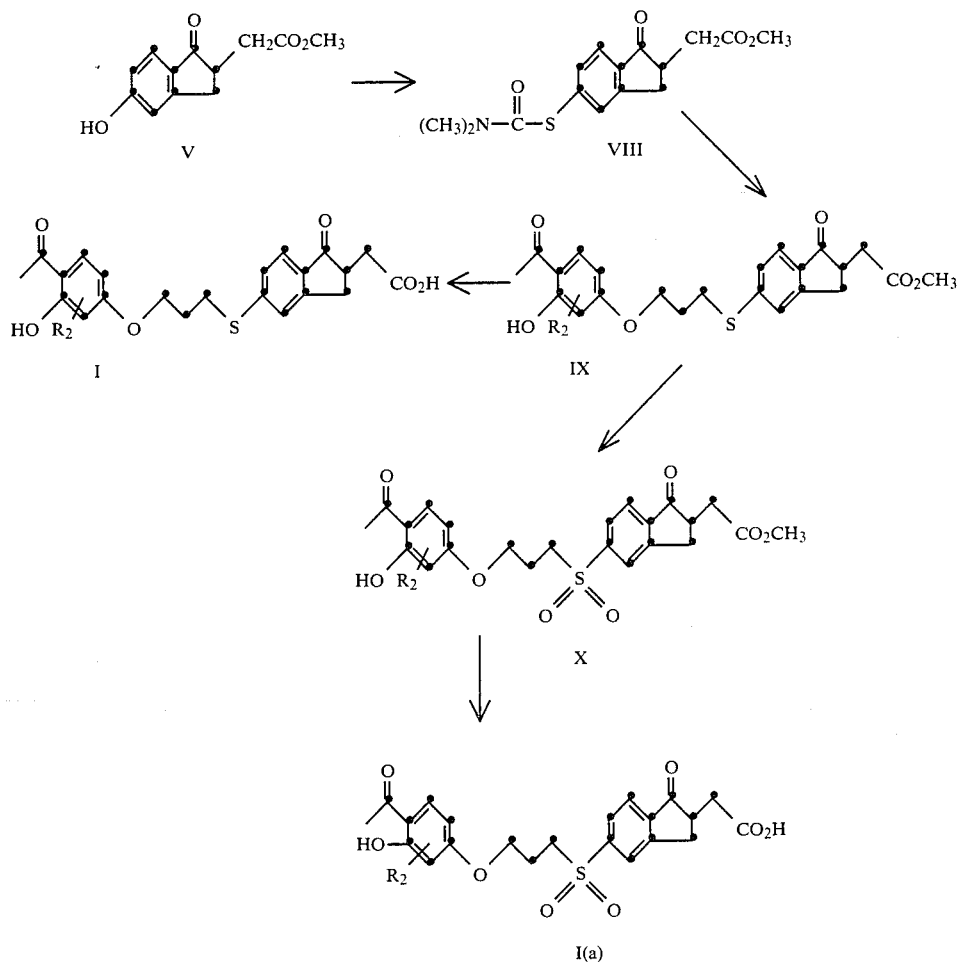

SCHEME II

An alternate preparation of I as illustrated in Scheme II involves the reaction of the thiol from formula VIII with a compound of formula VI under the conditions described in connection with Scheme I may be used to prepare the corresponding tetralones of the instant invention.

SCHEME III

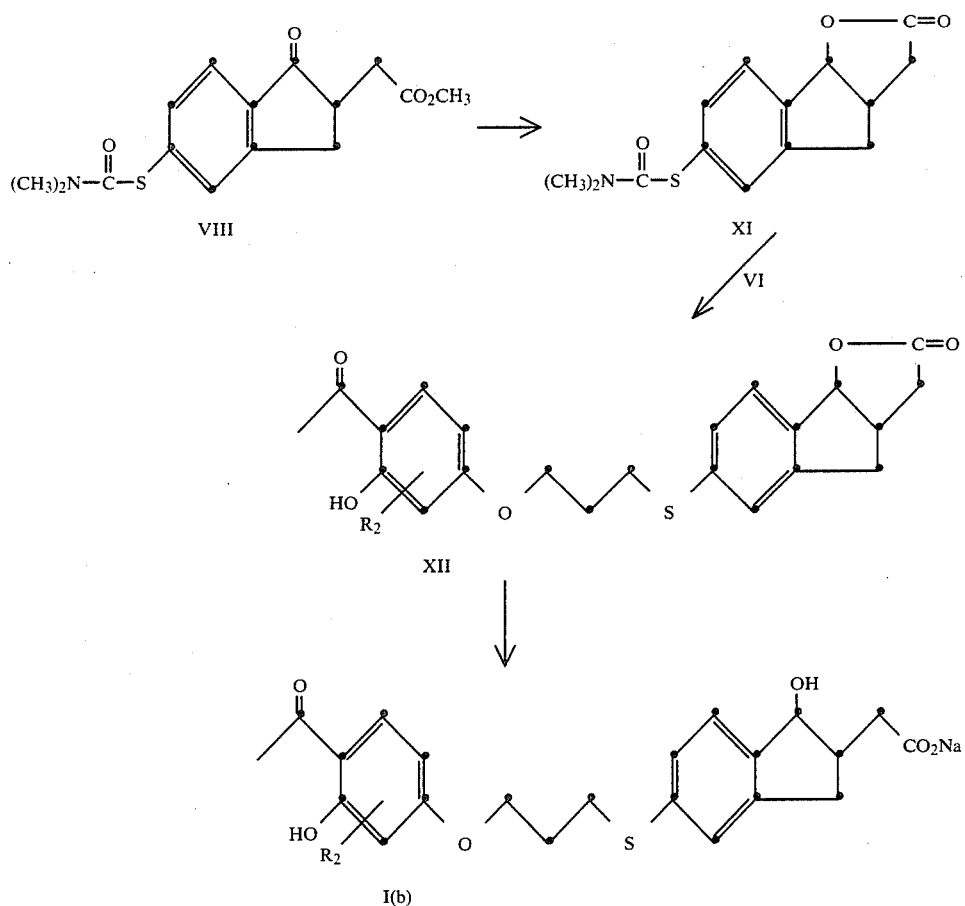

For the preparation of compounds of formula I where Z is OH, Scheme III is followed. Thus, reduction of the sodium salt prepared from the compound of formula VIII and 1N NaOH, with a reducing agent such as NaBH₄, gives rise, on acid work-up, to the gamma lactone of formula XI. Treatment of the gamma-lactone of formula XI as in Scheme III gives rise to the compound of formula XII. Base hydrolysis of the compound of formula XII, for example with 1N NaOH, affords the compound of formula I(b) wherein Z is OH.

In those instances when asymmetric carbon atoms are present, more than one stereoisomer is possible, and all possible isomeric forms are deemed to be included within the planar structural representations shown. Optically active (R) and (S) isomers may be resolved using conventional techniques known to the skilled artisan.

The cytoprotective activity of a compound may be observed in both animal and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanolinduced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosa are examined for resulting lesions.

B. Indomethacin-Induced Ulcer Assay

Indomethacin, 10 mg/kg p.o., is used to induce ulcers in 24 hour fasted S. K. rats. Fifteen minutes prior to indomethacin administration, groups of rats each receive either an aqueous vehicle (5% by weight methylcellulose) or the test compound at various doses perorally. Four hours later the animals are sacrificed and stomach mucosa are examined for resulting ulcers.

The magnitude of a prophylactic or therapeutic dose of a compound of formula I will, of course, vary with the nature of the severity of the condition to be treated and with the particular compound of formula I and its route of administration. In general, the daily dose range for anti-asthmatic, anti-allergic or anti-inflammatory use and, generally, uses other than cytoprotection lies within the range of from about 0.2 mg to about 100 mg to about 100 mg per kg body weight of a mammal. This dosage may be administered in single or divided individual doses.

As cytoprotective agents, the leukotriene antogonists of Formula I may generally be administered at a dosage range of 0.02 mg/kg to 100 mg.kg of body weight. The exact amount of inhibitor to be used will depend on, inter alia, whether it is being administered to heal damaged cells or to avoid future damage, on the nature of the damaged cells (e.g., gastro-intestinal ulcerations vs. nephrotic necrosis), and on the nature of the causative agent.

An example of the use of a compound of the Formula I in avoiding future damage would be coadministration of a compound of the Formula I with a non-steroidal anti-inflammatory drug (NSAID) that might otherwise cause such damage (for example, indomethacin). For such use, the compound of formula I is administered from 30 minutes prior up to 30 minutes after administration of NSAID. Preferably, it is administered prior to or simultaneously with the NSAID (for example in a combination dosage form).

The effective daily dosage level for compounds of Formulae I inducing cytoprotection in mammals, especially humans, will range from about 0.02 mg/kg to about 100 mg/kg, preferably from about 0.02 mg.kg to about 30 mg,kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed, dosage forms include tablets, troches, dispersions, suspensions, solutions, capsules and the like.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. For a helpful discussion of pharmaceutical salts see S. M. Berge et al., Journal of Pharmaceutical Sciences, 66, 1-19 (1977), the disclosure of which is hereby incorporated herein by reference.

The compositions of the present invention include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-imflammatory or anti-allergic use is from about 0.2 mg to about 20 mg (preferably from about 1 to about 10 mg) of a compound of Formula I per kg of body weight per day and for cytoprotective use from about 0.02 mg to about 30 (preferably from about 0.02 to about 20 of a compound of Formula I per kg of body weight per day. In the case where an oral composition is employed, a suitable dosage range for anti-asthmatic, anti-inflammatory or anti-allergic use is from about 1 to about 100 mg of a compound of Formula I per kg of body weight per day, preferably from about 5 mg to about 40 mg per kg and for cytoprotective use from about 0.1 mg to about 30 mg (preferably from about 0.1 mg to about 20 mg) of a compound of Formula I per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device In the case of a pressurized aerosol, the dosage unit may be determined by providing a valve to deliver a metered amount In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of the present invention:

| Injectable Suspension | mg/ml |
|---|---|
| Leukotriene antagonist | 2.0 |
| Methylcellulose | 5.0 |
| Tween 80 0.5 | |
| Benzyl alcohol | 9.0 |
| Methyl paraben | 1.8 |
| Propyl paraben | 0.2 |
| Water for injection to a total volume of 1 ml | |

| Tablet | mg/tablet |
|---|---|
| Leukotriene antagonist | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2.5 |
| | 500 |

| Capsule | mg/capsule |
|---|---|
| Leukotriene antagonist | 25.0 |
| Lactose Powder | 573.5 |
| Magnesium Stearate | 1.5 |
| | 600 |

In addition to the compounds of Formula I, the pharmaceutical compositions can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID, the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, aminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

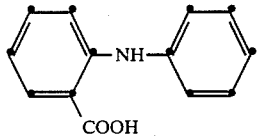

which can bear a variety of substituents and in which the free—COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/nonsteroidal anti-inflammatory drugs which contain the basic structure:

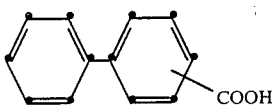

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

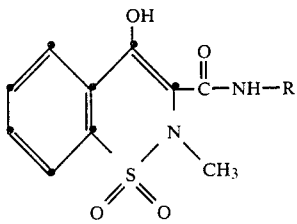

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, C0893XX, CPP, D10242, DKA9, DV17, EB382, EGYT2829 EL508, F1044, FZ, GP53633, GP650, GV3658, HG/3, ITCl, ITF, ITF182, KB1043, KC8973, KCNTEI6090, KME4, LA2851, LT696, LU20884, M7074, MED15, MG18311, MR714, MR897, MY309, N0164, ON03144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent application Ser. No. 539,342, filed Oct. 5, 1983, now abandoned, Ser. No. 459,924, filed Jan. 21, 1983, now abandoned, Ser. No. 539,215, filed Oct. 5, 1983, now abandoned, and Ser. No. 547,161, filed Oct. 31, 1983, now abandoned, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983, now both abandoned, which are hereby incorporated herein by reference and others known in the art such as those disclosed in European Patent Application Nos. 56, 172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, aminothiadiazoles disclosed in EP No. 81102976.8 and like compounds, such as those disclosed in U.S. Pat. Nos. 4,283,408; 4,362,736; 4,394,508; and European Patent Application No. 40,696 The pharmaceutical compositions may also contain a $K^+/H^+$ATPase inhibitor such as omeprazole, disclosed in U.S. Pat. No. 4,255,431, and the like. Each of the references referred to in this paragraph is hereby incorporated herein by reference.

The following examples illustrate the present invention without, however, limiting the same thereto. All temperatures are expressed in degrees Celsius.

EXAMPLE 1

Ethyl 5-methoxy-1-indanone-2-acetate

To a cooled (0° C.) solution of distilled diisopropylamine (8.3 ml) in dry THF (50 ml) was added 1.6 M n-BuLi/hexane (34 ml). The reaction mixture was stirred at room temperature under $N_2$ for 15 minutes as a cloudy yellow solution. Then the mixture was cooled at −78° C. (acetone/dry ice), and a solution of 5-methoxy-1-indanone (8 g) in dry THF (100 ml) was slowly added under $N_2$. A solid formed after complete addition. The mixture was stirred at −78° C. under $N_2$ for 40 minutes. To this mixture was added dropwise ethyl bromoacetate (6.6 ml) and the mixture was slowly brought to room temperature and stirred overnight at room temperature under $N_2$ as a dark homogenous solution. The reaction mixture was poured into a mixture of H$_2$O (500 ml), ice and conc. HCl. The mixture was extracted with Et$_2$O (3X). The combined organic layers were washed with H$_2$O, dried and evaporated to give an oil. Chromatography of the oil on a column of silica gel (70–230 mesh, 200 g) using hexane/EtOAc as eluant gave the title compound.

EXAMPLE 2

Methyl 5-hydroxy-1-indanone-2-acetate

A mixture of the compound of Example 1 (8.0 g), acetic acid (30 ml) and 48% HBr (150 ml) was refluxed overnight to afford a dark solution. The reaction mixture was cooled to room temperature and poured into a mixture of H$_2$O and ice (500 ml) and extracted with EtOAc (3X). The combined organic layers were washed with H$_2$O (3X), dried and evaporated to give a pink solid. The pink solid was suspended in methanol (20 ml), 10% HCl/MeOH (80 ml) was added and the reaction mixture was stirred overnight at room temperature. The reaction mixture was evaporated to yield the title compound as a pink solid, m.p. 146°–150°.

EXAMPLE 3

Methyl 5-(3-(4-acetyl-3-hydroxy-2-n-propylphenoxy)-propyloxy)-1-indanone-2-acetate To a solution of 2-hydroxy-3-propyl-4(3-bromopropoxy)acetophenone (1.1 g) and the compound of Example 2 (640 mg) in methyl ethyl ketone (30 ml) was added potassium carbonate (1.20 g). The resulting mixture was heated at reflux overnight. The reaction mixture was cooled to room temperature, filtered and the filtrate was evaporated.

The residue was chromatographed on column of silica gel (70-230 mesh, 100 g) and eluted with toluene/EtOAc (10:2) to give the title compound. Purification by HPLC afforded a white solid, m.p. 64°–66°.

EXAMPLE 4

5-(3-(4-acetyl-3-hydroxy-2-n-propylphenoxy)propyl-oxy)-1-indanone-2-acetic acid

To a solution of the ester from Example 3 (830 mg) in THF (25 ml) was added 1N NaOH (5.5 ml) and MeOH (2 ml). The mixture was stirred at room temperature for 2 hours. The reaction mixture was diluted with H$_2$O (200 ml), acidified with conc. HCl and extracted with EtOAc (3X). The combined organic extracts were washed with brine, dried and evaporated to give an oil. Purification of the oil on a column of silica gel (70–230 mesh, 50 g) eluting with toluene/dioxane/AcOH (10:2:0.1) gave the title compound as a beige solid, m.p. 132°–134°.

Analysis, calculated: C, 68.17; H, 6.41. Found: C, 68.17; H, 6.42.

EXAMPLE 5

Methyl 5-(N,N-dimethylcarbamylthio)-1-indanone-2-acetate

A solution of the compound of Example 2 (4.4 g) and dimethylthiocarbamoyl chloride (3.0 g) in pyridine (20 ml) was refluxed in an atmosphere of N$_2$ for 5 hours and cooled. The crude reaction mixture was poured into ice-water (500 ml), extracted with ether (200 ml×3). The combined organic extracts were washed with 0.1N HCl, brine and concentrated. The residual oil in CH$_2$Cl$_2$ was washed with brine and dried over Na$_2$SO$_4$. After concentration in vacuo, the residual oil was heated (neat) at 200° C. for 12 hours. Purification of the resulting solid by HPLC, eluting with hexane/EtOAc (1:1), gave the title compound as an oil which crystallized when triturated with ether, m.p. 82°–84°.

EXAMPLE 6

Methyl 5-(3-(4-acetyl-3-hydroxy-2-n-propylphenoxy) propylthio)-1-indanone-2-acetate To a solution of sodium (0.5 g) in MeOH (20 ml) at 0° was added the thiocarbamate of Example 5(2.0 g) in one portion. The mixture was stirred at room temperature for 18 hours. 2-Hydroxy-3-propyl-4-(3-bromopropoxy)acetophenone (2.1 g) was added and the mixture was stirred at room temperature for 8 hours. The reaction mixture was cooled to −20° C., poured into crushed ice, acidified with 1N HCl and extracted with CH$_2$Cl$_2$. The extracts were washed with brine and the acidic material was extracted into 0.1 1N NaOH, reacidified with 1N HCl and extracted with CH$_2$Cl$_2$ to yield Fraction A. The neutral material was washed with brine, dried over Na$_2$SO$_4$, to yield Fraction B which was chromatographed on a column of silica gel (20–230 mesh, 100 g) eluting with (10:3) hexane-EtOAc then (2:1) hexane-EtOAc to give the title ester as a solid, m.p. 73°–75° C.

Fraction A was esterified with MeOH-HCl (gas) at room temperature overnight and similarly chromatographed to give the title ester.

EXAMPLE 7

5-(3-(4-acetyl-3-hydroxy-2-n-propylphenoxy)propylthio)-1-indanone-2-acetic acid

The ester of Example 6 (896 mg) was hydrolyzed at room temperature using 1N NaOH (5.7 ml) in THF (25 ml) for 2 hours and evaporated in vacuo at 30°. The residual aqueous layer was acidified with 1N HCl in an ice-bath. Extraction with EtOAc gave an oil which was crystallized from ether to give the title compound, m.p. 125°–128°.

Analysis, calculated: C, 65.77; H, 6.18; S, 7.02. Found: C, 65.76; H, 6.24; S, 7.20.

EXAMPLE 8

Methyl 5-(3-(4-acetyl-3-hydroxy-2-n-propylphenoxy) propylsulfonyl)-1-indanone-2-acetate To a solution of the ester of Example 6 (780 mg) in CH$_2$Cl$_2$ (10 ml) at 0° was added a solution of m-CPBA (900 mg) in CH$_2$Cl$_2$ (20 ml). The solution was stirred at room temperature for 20 minutes, Ca(OH)$_2$ (1g) was added and the mixture was filtered. Removal of the solvent gave an oil and chromatography on a column of silica gel, eluting with hexane-EtOAc (1:1), gave the title compound as crystals, m.p. 97°–100°.

EXAMPLE 9

5-(3-(4-acetyl-3-hydroxy-2-n-propylphenoxy)propylsulfonyl)-1-indanone-2-acetic acid The ester of Example 8 (692 mg) was hydrolyzed at room temperature for 2 hours using 1N NaOH (4.2 ml) in THF (20 ml). The reaction mixture was acidified and extracted with EtOAc (50 ml×3).

The combined organic extracts were washed wtih brine, dried and concentrated in vacuo to give the title compound, m.p. 170°–173°, after recrystallization from ether. Analysis, calculated: C, 61.46; H, 5.78; S, 6.56. Found: C, 61.37; H, 5.92; S, 6.50.

EXAMPLE 10

5-(N,N-dimethylcarbamylthio)-1-hydroxyindane-2-acetic acid gamma lactone

To a solution of the thiocarbamate ketoester of Example 5 (615 mg) in THF (3 ml) was added 1N NaOH (2.5 ml) and MeOH (0.5 ml) and the mixture was stirred at room temperature for 1 hour. To the resulting sodium salt in solution were added successively 40 mg of NaBH4 and 1 mg of CeCl3 at 0°. (H2 gas was evolved.) The mixture was stirred at 0° for 20 minutes and acidified with 1N HCl. Extraction with ether gave colorless solids. To the solid dissolved in $CH_2Cl_2$ was added trifluoroacetic acid (TFA) (2 drops) and the solution was stirred for 12 hours at room temperature. The solution was washed with aqueous bicarbonate, brine and dried over $Na_2SO_4$ to give the title compound as an oil. NMR (CDCl3) (ppm): 2.37 (1H, dd, J=18 and 5 Hz), 2.67–3.53 (10 H), 5.87 (1H, d, J=7Hz), 7.47 (3H, m).

EXAMPLE 11

5-(3-(4-acetyl-3-hydroxy-2-n-propylphenoxy)propylthio)-1-hydroxy-indane-2-acetic acid gamma lactone To a solution of the compound of Example 10 (280 mg) in MeOH (10 ml) was added 2N NaOH (5 ml) and the solution was refluxed in an atmosphere of argon for 15 hours. The mixture was cooled and 2-hydroxy-3-propyl-4-(3-bromopropoxy)acetophenone (473 mg) was added at 20° and the mixture was stirred at 20° for 0.5 hours then refluxed for 4 hours. The mixture was cooled, poured into ice, acidified with 6N HCl and extracted with $CH_2Cl_2$. The combined extracts were concentrated, and the residue redissolved in 20 ml of $CH_2Cl_2$ and treated with 5 drops of TFA at 20° C. for 15 minutes. The solution was washed with brine, dried over $Na_2SO_4$ and concentrated in vacuo. Chromatography in a column of silica gel(20–230 mesh) eluting with EtOAc-hexane (1:1) gave the title compound as an oil.

NMR (CDCl3) (ppm): 0.93 (3H, t), 1.55 (2H, m), 2.20 (2H, m), 2.37–3.53 (12 H, including 3H singlet at 2.55), 4.15 (2H, t), 5.83 (1H, d, J=7 Hz), 6.43 (1H, d, J=9 Hz), 7.30 (3H, m), 7.63 (1H, d, J=9 Hz), 12.83 (1H, exchangeable in D2O).

EXAMPLE 12

5-(3-(4-acetyl-3-hydroxy-2-n-propylphenoxy)propylthio)-1-hydroxy-indane-2-acetic acid sodium salt A solution of the gamma-lactone from Example 11 (230 mg) in THF (5 ml), 1N NaOH (0.8 ml) and MeOH (1 ml) was stirred at 20° for 12 hour and concen-trated to dryness. The residue, dissolved in H2O, was passed through an XAD-8 column (eluting first with H2O then with 95% EtOH). The fractions containing the title salt were collected and concentrated to dryness.

Analysis, calculated: C, 62.48; H, 6.08; S, 6.67. Found: C, 62.52; H, 6.05; S, 6.67.

EXAMPLE 13

Methyl 6-methoxy-1-tetralone-2-acetate

To a solution of LDA, prepared from diisopropylamine (0.84 ml) and n-butyl lithium (3.44 ml, 1.6 M in hexane) in 10 ml of THF at −78° was added dropwise a solution of 6-methoxy-1-tetralone (0.88 g, 5.0 mmol) in 5 ml of THF in an atmosphere of nitrogen. To the stirred solution at −78° was then added methyl bromoacetate (0.5 ml, 6.0 mmole) and the mixture was allowed to warm to room temperature. Aqueous work-up and extraction with ether gave, after chromatography on silica gel, the title compound, m.p. 110°–112°.

EXAMPLE 14

Methyl 6-hydroxy-1-tetralone-2-acetate

A solution of the 6-methoxy-1-tetralone derivative (860 mg) (from Example 13) in 47% HBr (15 ml) and glacial acetic acid (5 ml) was refluxed for 30 hours and poured into ice-water. The product was extracted into ethyl acetate (3X) and the combined organic extracts were washed with brine, dried over $Na_2SO_4$ and concentrated to dryness. The residue was esterified with 10% HCl in methanol to give, after work-up, the title compound, m.p. 121°–123°.

EXAMPLE 15

Methyl 6-(N,N-dimethylcarbamylthio)-1-tetralone-2-acetate

Following the procedure of Example 5, but substituting the compound of Example 14 for methyl -hydroxy-1-indanone-2-acetate, the title compound is obtained.

EXAMPLE 16

Methyl 6-(3-(4-acetyl-3-hydroxy-2-n-propylphenoxy)propylthio)-1-tetralone-2-acetate Following the procedure of Example 6, but substituting the compound of Example 15 for the compound of Example 5, the title compound is obtained.

EXAMPLE 17

6-(3-(4-Acetyl-3-hydroxy-2-n-propyl phenoxy)propylthio)-1-tetralone-2-acetic acid Following the procedure of Example 7, but substituting the compound of Example 16 for the compound of Example 6, the title compound is obtained.

EXAMPLE 18

Methyl 6-(3-(4-acetyl-3-hydroxy-2-n-propylphenoxy)propyloxy)-1-tetralone-2-acetate Following the procedure of Example 3, but substituting the compound of Example 14 for methyl 5-hydroxy-1-indanone-2-acetate, the title compound was obtained as a solid, m.p. 96°–98°.

Analysis, calculated: C, 69.21; H, 6.89. Found: C, 69.08; H, 6.93.

EXAMPLE 19

6-(3-(4-acetyl-3-hydroxy-2-n-propylphenoxy)-propyloxy)--tetralone-2- acetic acid Following the procedure of Example 4, but substituting the compound of Example 18 for the compound of Example 3, the title compound was obtained as a solid, m.p. 123°–125°.

Analysis, calculated: C, 68.70; H, 6.65. Found: C, 68.95; H, 6.70.

EXAMPLE 20

Methyl 5-(3-bromopropyloxy)-1-indanone-2-acetate

A mixture of 1,3-dibromopropane (15 ml), the compound of Example 2 (8.0 g) and potassium carbonate (15.0 g) in methyl ethyl ketone (45 ml) was heated at reflux overnight. The reaction mixture was filtered through a bed of Celite and the filtrate was concentrated in vacuo. The residue was chromatographed on a column of silica gel (70–230 mesh, 200 g) eluting with hexane/EtOAc (5:2) to give the title compound as an oil.

NMR (CDCl$_3$) (ppm): 2.2–3.5 (7H, m), 3.60 (2H, t, J =6 Hz), 3.67 (3H, s), 4.17 (2H, t, J =6 Hz), 6.80–7.00 (2H, m), 7.65 (1H, d, (J =9 Hz).

EXAMPLE 21

5-(3-Bromopropyloxy)-1-hydroxyindane-2-acetic acid gamma lactone

To a solution of the compound of Example 20 (8.7 g) and cerium (III) chloride (50 mg) in methanol (60 ml) at 0° C. was added sodium borohydride (1.23 g). The reaction mixture was stirred at 0° C. for 30 minutes, acidified with 1N HCl and the resulting solid material was collected by filtration. The solid material was dissolved in methanol (2 ml) and THF (10 ml), and 1N NaOH (31 ml) was added. The mixture was stirred at room temperature for 3 hours and acidified with 1N HCl. The product was extracted into dichloromethane (100 ml×3), washed with brine and dried over anhydrous sodium sulfate. The solvent was removed in vacuo and the residue in dichloromethane (30 ml) was treated with 5 drops of trifluoroacetic acid for 5 minutes. The solution was washed with saturated aqueous sodium bicarbonate, brine and dried over anhydrous sodium sulfate. Removal of the solvent gave the title compound as an oil.

NMR (CDCl$_3$) (ppm): 2.20–2.45 (3H, m), 2.80–2.95 (2H, m), 3.20–3.45 (2H, m), 3.60 (2H, t, J =6 Hz), 4.10 (2H, t, J =6 Hz), 5.82 (1H, d, J =6 Hz), 6.77–6.90 (2H, m), 7.35 (1H, d, J =8 Hz).

EXAMPLE 22

5-(3-(4-acetyl-3-hydroxy-2-n-propylphenoxy)propyloxy)-1-hydroxyindane-2- acetic acid gamma lactone A mixture of the compound of Example 21 (3.11 g), 2,4-dihydroxy-3-n-propylacetophenone (1.94 g) and potassium carbonate (2.76 g) in methyl ethyl ketone (40 ml) was refluxed for 6 hours. The reaction mixture was filtered and the filtrate was concentrated in vacuo. The residue was chromatographed on a column of silica gel (70–230 mesh, 100 g) eluting with hexane/EtOAc (1:1) to give the title compound as a solid, m.p. 96°–97°.

Analysis calculated: C, 70.74; H, 6.65.
Found: C, 70.56; H, 6.51.

EXAMPLE 23

5-(3-(4-Acetyl-3-hydroxy-2-n-propylphenoxy)-propyloxy)-1-hydroxyindane -2-acetic acid sodium salt Following the procedure of Example 12, but substituting the compound of Example 22 for the compound of Example 11, the title compound was obtained as a solid, m.p. 156°–159°.

Analysis, calculated: C, 64.64; H, 6.29
Found: C, 64.32; H, 6.22.

Claims to the invention follow.

What is claimed is:

1. Methyl 5-(3-(4-acetyl-3-hydroxy-2-n-propylphenoxy)propyloxy) -1-indanone-2-acetate.

2. 5-(3-(4-Acetyl-3-hydroxy-2-n-propylphenoxy)-propyloxy)-1-indanone-2-acetic acid.

3. Methyl 5-(3-(4-acetyl-3-hydroxy-2n-propylphenoxy)-propylsulfonyl)-1-indanone-2-acetate.

4. 5-(3-(4-Acetyl-3-hydroxy-2-n-propylphenoxy)-propylsulfonyl)-1-indanone-2-acetic.

5. Methyl 5-(3-(4-acetyl-3-hydroxy-2-n-propylphenoxy)propylthio)-1-indanone-2-acetate.

6. 5-(3-(4-Acetyl-3-hydroxy-2-n-propylphenoxy)propyl-thio)-1-indanone-2-acetic acid.

7. 5-(3-(4-acetyl-3-hydroxy-2-n-propylphenoxy)propyl-thio)-1-hydroxy-indane-2-acetic acid sodium salt.

8. Methyl 6-(3-(4-acetyl-3-hydroxy-2-n-propylphenoxy)propylthio)-1-tetralone-2-acetate.

9. 6-(3-(4-Acetyl-3-hydroxy-2-n-propyl phenoxy) propyl-thio)-1-tetralone-2-acetic acid.

10. Methyl 6-(3-(4-acetyl-3hydroxy-2-n-propylphenoxy)-propyloxy)-1-tetralone-2-acetate.

11. 6-(3-(4-acetyl-3-hydroxy-2-n-propylphenoxy)-propyloxy)-1-tetralone-2-acetic acid.

12. 5-(3-(4-acetyl-3-hydroxy-2-n-propylphenoxy)-propyloxy)-1-hydroxyindane-2-acetic-acid sodium salt.

* * * * *